(12) United States Patent
Malak

(10) Patent No.: US 6,336,925 B1
(45) Date of Patent: Jan. 8, 2002

(54) LIPOSUCTION APPARATUS

(76) Inventor: Jean Malak, rue de Versailles 2, 7130 Binche (BE)

(*) Notice: Subject to any disclaimer, the term of this patent is extended or adjusted under 35 U.S.C. 154(b) by 0 days.

(21) Appl. No.: 09/402,372
(22) PCT Filed: Apr. 2, 1998
(86) PCT No.: PCT/BE98/00047
§ 371 Date: Oct. 4, 1999
§ 102(e) Date: Oct. 4, 1999
(87) PCT Pub. No.: WO98/44966
PCT Pub. Date: Oct. 15, 1998

(30) Foreign Application Priority Data

Apr. 3, 1997 (BE) .......................................... 09700305

(51) Int. Cl.⁷ ................................................ A61M 1/00
(52) U.S. Cl. ............................ 604/542; 604/22; 604/35
(58) Field of Search ............................ 604/22, 27, 35, 604/43, 152, 156, 157, 542, 902

(56) References Cited

U.S. PATENT DOCUMENTS

| | | | |
|---|---|---|---|
| 4,735,604 A | | 4/1988 | Watmough et al. |
| 4,863,439 A | | 9/1989 | Sanderson |
| 5,123,903 A | * | 6/1992 | Quaid et al. ................... 604/22 |
| 5,348,535 A | | 9/1994 | Cucin |
| 5,352,194 A | * | 10/1994 | Greco et al. ............. 604/902 X |
| 5,514,086 A | * | 5/1996 | Parisi et al. ................... 604/22 |
| 6,113,569 A | * | 9/2000 | Becker ................... 604/542 X |

FOREIGN PATENT DOCUMENTS

| | | |
|---|---|---|
| DE | 33 13325 A1 | 10/1984 |
| FR | 2 559 066 A1 | 8/1985 |
| FR | 2 648 050 A1 | 12/1990 |
| FR | 2 691 624 A1 | 12/1993 |
| WO | WO 93/02627 | 2/1993 |

* cited by examiner

Primary Examiner—Anhtuan T. Nguyen
(74) Attorney, Agent, or Firm—Venable; Ashley J. Wells

(57) ABSTRACT

A liposuction device including sucking cannula member for sucking subcutaneous fat through an entry aperture, the sucking cannula member having defined therein said entry aperture and having a longitudinal axis; mechanical drive member for producing and transmitting a movement to the sucking cannula member and on which the sucking cannula member is mounted, the mechanical drive member having an entry for connecting an energy source thereto, and the movement of the sucking cannula member being a nutational movement which has a frequency ranging from 10 to 500 Hz and which comprises a vibrational component and a translational component, the vibrational component being perpendicular to the longitudinal axis of the sucking cannula member and the translational component being in line with the longitudinal axis of the sucking cannula member and having an amplitude ranging from 2 mm up to but less than 1 cm; a housing for housing the mechanical drive member; and a free space provided between the sucking cannula member and the housing, the free space being dimensioned to allow the vibrational component of the nutational movement to dislocate subcutaneous fat in use.

10 Claims, 7 Drawing Sheets

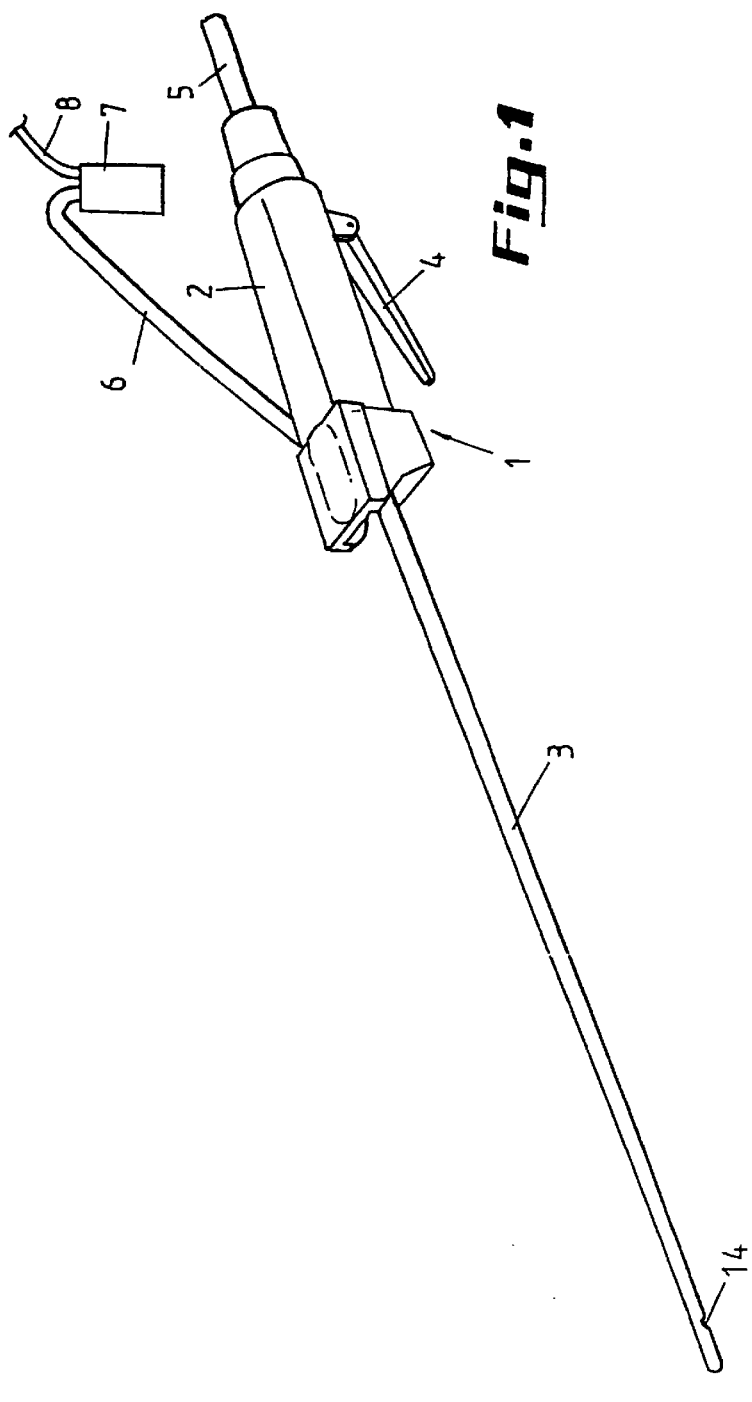
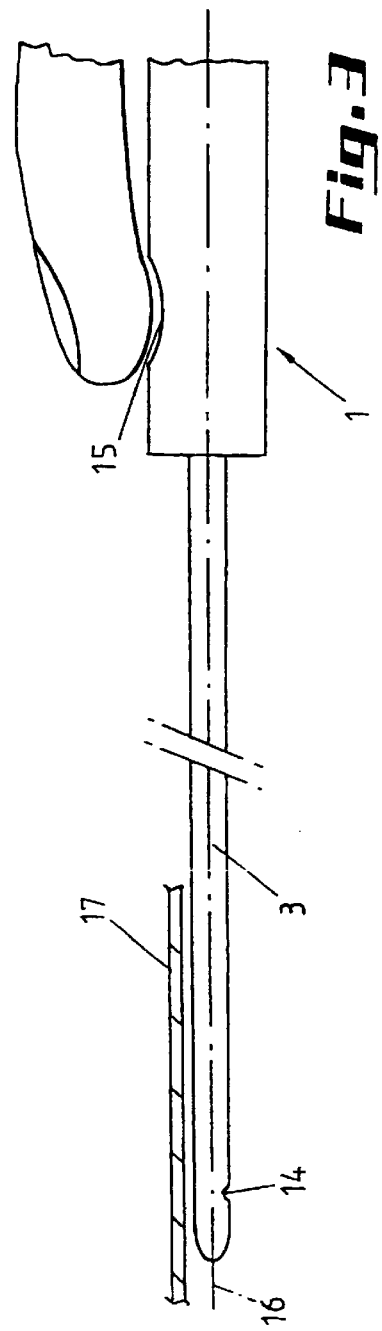

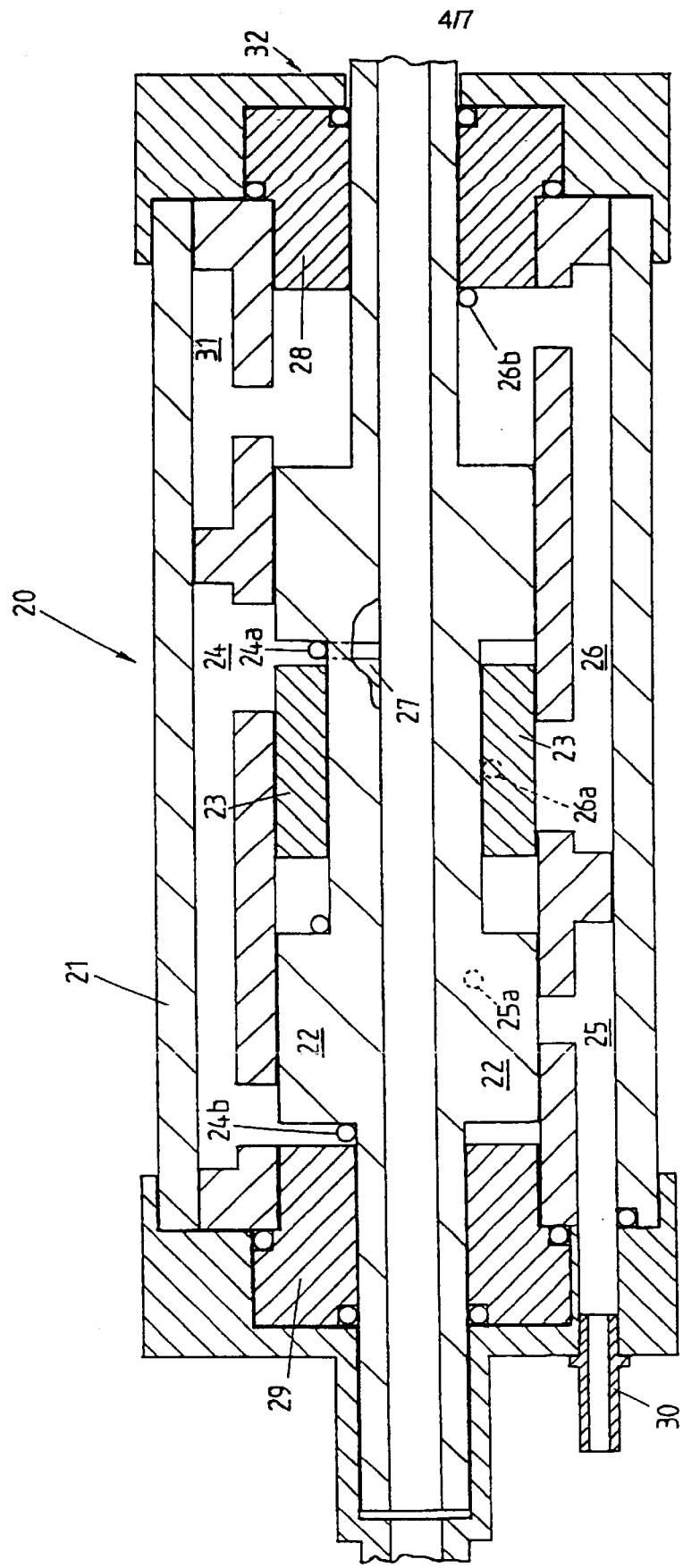

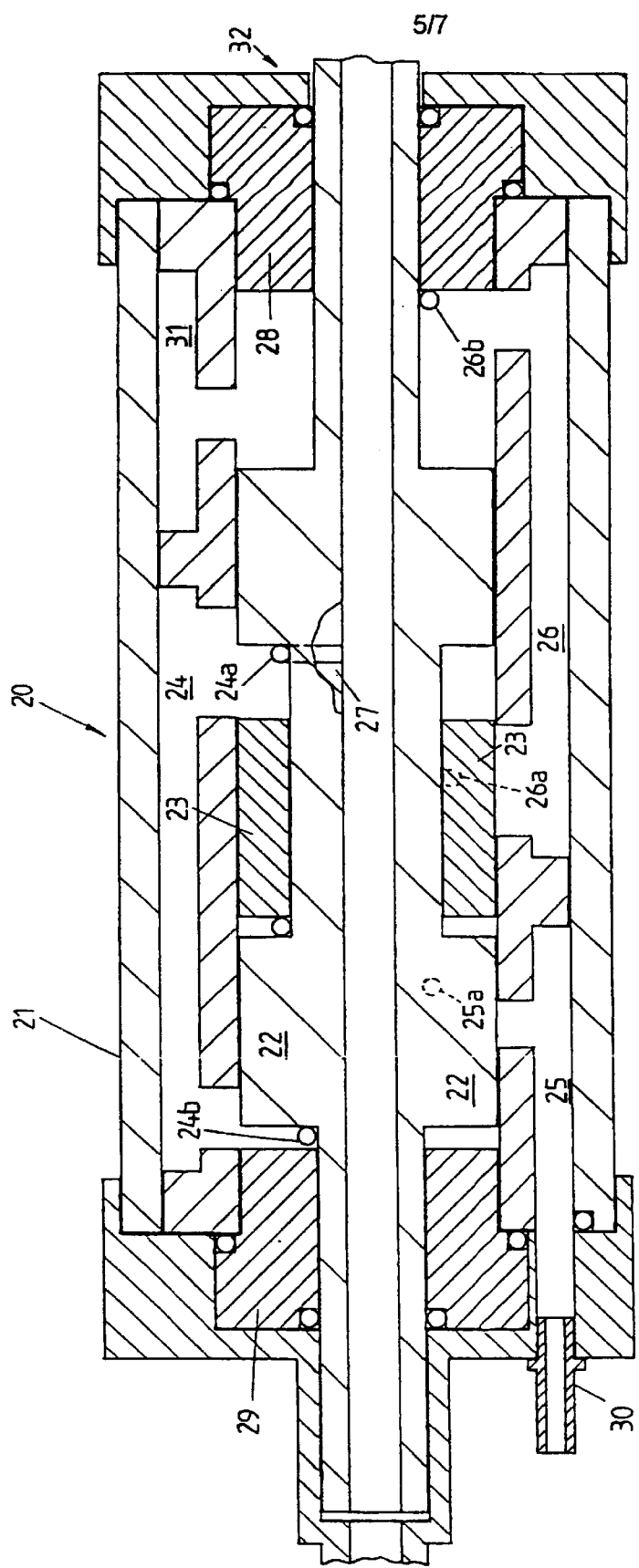

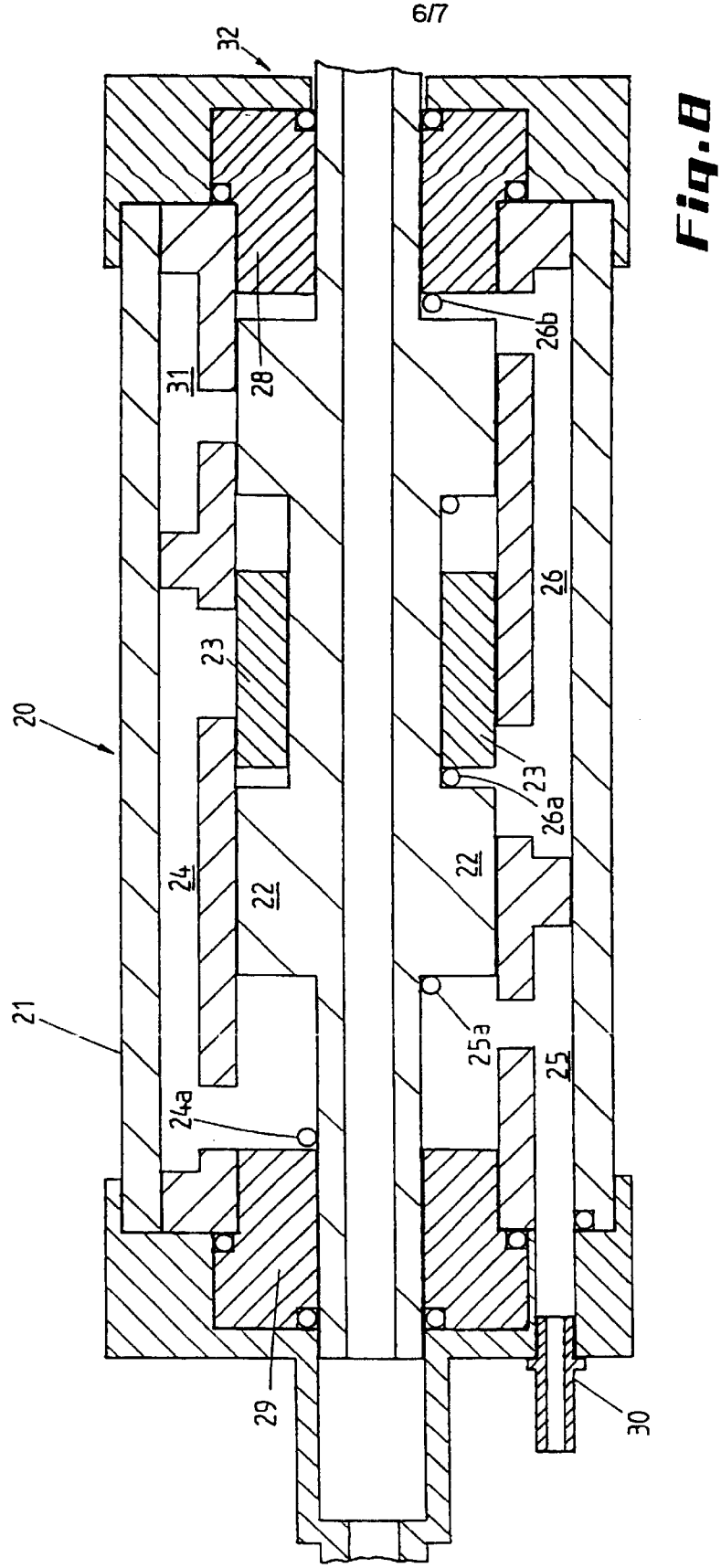

LIPOSUCTION APPARATUS

BACKGROUND OF THE INVENTION

1. Field of the Invention

The present invention relates to a liposuction device comprising a suction cannula provided for sucking in subcutaneous fat through an entry aperture, the cannula having a longitudinal axis and being mounted on a mechanical drive member having an input provided for connecting an energy source and for producing and transmitting a movement to said cannula.

2. Description of the Related Art

The technique itself of liposuction is known as such. The suction cannula is provided to be introduced under the skin of the patient. The cannula is driven to the zone where the fat must be sucked in. The suction of the fat itself is accompanied with a repeated backward and forward motion and with a depression created inside the cannula.

To assist the user during the liposuction, apparatus with mechanical assistance have been developed provided with a mechanical drive member for producing and transmitting a movement to the cannula. In these devices, such as for example described in U.S. Pat. No. 5,348,535, the produced movement is a translation movement applied to a scrape member. In order to guide the translation movement from this member, these devices comprise an inner cannula sliding within an outer guiding cannula. The outer cannula is thus provided for guiding the translation movement from the inner cannula, whereas the inner cannula serves as suction cannula.

The drawback of the device according to U.S. Pat. No. 5,438,535 is that the translation movement of the inner cannula with respect to the outer cannula provokes a "guillotine" or cutting effect, i.e. it may provoke the cut of the vessels and the nerves. This guillotine effect almost necessarily imposes a general anesthesia of the patient. Furthermore, the fat risks to infiltrate between the inner cannula and the outer cannula, which can provoke a blocking of the translation movement. The known device has also the inconvenient that, due to the presence of a double cannula, i.e. an inner cannula sliding within an outer cannula, the diameter of the cannula is relatively high. If one wishes to reduce the diameter of the outer cannula for allowing to access more easily within the body of the patient, the diameter of the inner cannula will also be reduced, which reduces the fat suction flow.

Another liposuction device is described in U.S. Pat. No. 5,352,194. The drive member of this device is provided for producing a translation movement having an amplitude of at least 1 cm. Such an amplitude produces a scrape effect which is dangerous since the user risks to exceed the limits of the region to be liposucked and injures in this way the patient. Furthermore, the larger the amplitude, the larger the reaction will be, which continuously provokes the back motion of the user's wrist and reduces in this way the precision of the accomplished work.

Another liposuction device is described in patent application FR 2,691,624. This device is an ultrasound device, wherein the drive member is provided for producing a vibration movement at ultrasound frequency. Such a device turned out to be not very efficient, since the vibration movement at ultrasound frequency has to dispose the fat cells for subsequent suction. This technique is very slow. In addition, serious burns and cutaneous necrosis can occur.

The object of the present invention is to realise a liposuction device the use of which causes considerably less damage on the vessels and nerves, while achieving a mechanical assistance which allows to remove efficiently subcutaneous fat of the patient.

SUMMARY OF THE INVENTION

To this object, the liposuction device according to the invention is characterized in that the movement of the cannula is a nutation movement comprising vibration component perpendicular to the axis of the cannula and a translation component according to the axis of the cannula, wherein the translation component has an amplitude less than 1 cm.

The transmission of such nutation movement to the cannula has a double effect. On the one hand, the vibration component allows the cannula to perform a vibration movement when the latter is situated in the subcutaneous fat tissue. This movement will induce a vibration in the fat, allowing to easily introduce the fat in the cannula. On the other hand, the translation component amplifies the vibration component and insures in this way an efficient liposuction. The translation movement allows also to progress very easily and more smoothly the cannula within the skin of the patient. Limiting the amplitude of the translation component to a value less then 1 cm, the fat can easily be sucked in within its expansion limit while limiting considerably the risk to exceed the zone to be treated. The movement transmitted by the drive member creates a sinusoidal wave which extends along the cannula provoking a nutation force which contributes to dislocate the fat and to realize a real emulsion of the fatty tissue.

It has been established during experiments that a little amount of blood was extracted through the cannula, clearly indicating that the liposuction performed with the device according to the invention considerably limits vessels and nerves lesions compared to known devices with mechanical assistance, wherein there is either a guillotine effect or a scrape effect, or an inefficient liposuction. A local aneasthesia is therefore sufficient. Due to the absence of two cannulas sliding within one another, the diameter of the cannula introduced under the skin of the patient can be relatively limited, allowing to access more easily to zones of the human body having a relatively restricted access, such as the chin and the ankle, and limits furthermore the dimensions of scars formed on the skin of the patient.

In a first preferred embodiment of a device according to the invention, said movement produced by the drive member has a frequency between 10 and 500 Hz, preferably less than 250 Hz and most preferably approximately equal to 15 Hz. It has been found that such a frequency range allows to obtain efficient results in combination with the translation movement having an amplitude of less than 1 cm.

In a second preferred embodiment, the device according to the invention comprises a handle wherein said drive member is housed. This facilitates handling of the device according to the invention.

Preferably, the device comprises in addition a control member provided to control starting and stopping the drive member. In particular, the control member is a switch housed in said handle, or is formed by a control pedal cooperating with said drive member. The user can in this way easily control starting and stopping the device, in particular by controlling and holding the device with the same hand or by controlling the device by means of one of his feet.

Preferably said drive member is provided for functioning with compressed air and comprises a pneumatic piston for producing a backward and forward motion. The use of compressed air allows to realize a device which is easy to sterilize.

In another preferred embodiment of the liposuction device according to the invention, the device comprises in addition a cavity for a thumb, said cavity and said aperture being positioned on either side of the cannula axis. This embodiment allows the entry aperture to be directed towards the depth of fatty tissue and not towards the skin of the patient when the operator has introduced the cannula under the skin of a patient and has placed his thumb within the cavity.

BRIEF DESCRIPTION OF THE DRAWINGS

The invention will now be described more in detail by means of the drawings illustrating an example of the device according to the invention. In the drawings:

FIG. 1 illustrates an overall assembly of a liposuction device according to the invention.

FIG. 3 illustrates a portion of a preferred embodiment of the device according to the invention.

FIGS. 6 to 8 illustrate a section view of different working phases of a motor allowing to produce the movement to be imposed to the cannula.

In the drawings, a same reference numeral is assigned to same or analogous elements.

DESCRIPTION OF THE PREFERRED EMBODIMENTS

Figure 2:
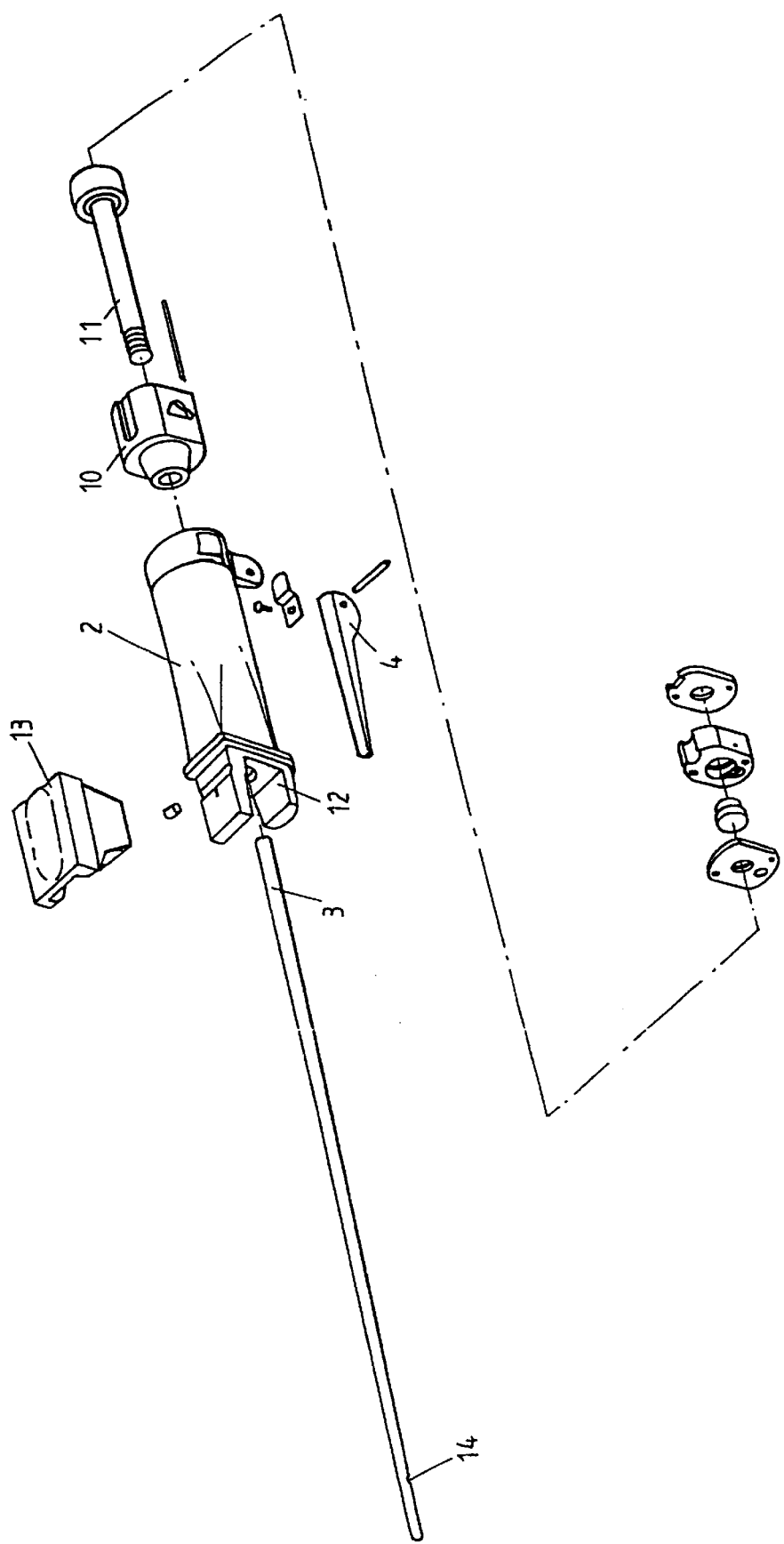
FIG. 2 illustrates the principal components of a device according to the invention.

FIG. 1 shows an example of an embodiment of a liposuction device according to the invention. In the shown example, the device uses compressed gas, preferably compressed air, in particular sterile dehydrated medical air, as energy source. Due to the medical use, the device with compressed air has the advantage to be easily sterilized. Other sources of energy can however be used such as electric current, magnetic induction or a liquid under pressure. The advantage however to use compressed air compared to electrical current is that it avoids overheating of the device to a considerable extent when the movement is blocked, for example due to a block up of the cannula.

The liposuction device 1 comprises a housing 2 which forms at the same time the handle of the device. Inside the housing, a mechanical drive member is housed to which the sucking cannula 3 is connected, said cannula presenting at least one aperture 14. The cannula 3 has preferably a diameter in the order of 1.5 to 6 mm, in particular approximately 3, 4 or 5 mm, in function of the fat layer to be sucked in. This limited diameter allows an easy access to locations of the human body. The cannula has a smooth surface and is preferably coated with a layer of Teflon®. The apertures 14 are preferably 1 to 3 in number having a diameter of 2 to 5 mm, the apertures being preferably located at the height of the free end of the cannula. The compressed gas is provided by means of a conduct 5 connectable to a source of compressed gas. Cannula 3 is connected through the housing to a discharge conduct 6 which ends in a collector 7 of the sucked fat through the cannula. The collector 7 is also connected through a conduct 8 connected to a unit (not shown in the drawing) provided for creating a depression inside the cannula, as for example a vacuum cleaner.

The housing 2 comprises also a control member, for example a switch 4, which controls starting and stopping of the drive member. According to another embodiment, a control pedal is provided for starting and stopping the device. Preferably, the control member 4 controls also the suction source which causes the depression inside the cannula. In this way, the user can control with one and same movement the entire functioning of the device according to the invention.

According to a first embodiment, the drive member located inside the housing, comprises a cylinder 10 and a pneumatic piston 11 driven by the compressed gas provided through conduct 5. The piston 11 acts on the cannula 3 which is connected to the piston 11. A protection cap 13 protects the exit of the cannula at the height of the handle. Preferably, the pressure of the compressed gas is set between 1 to 5 bar in function of the hardness of the fat to be sucked. For a fat harder or more fibrous, one will tend to use a pressure of 4 to 5 bar, whereas for a more soft and less fibrous fat, one will tend to choose a pressure of less than 4 bar.

Preferably, as illustrated in FIG. 3, the handle presents a cavity 15 provided for placing the user's thumb, said cavity 15 and said aperture 14 being positioned at each side of the axis 16 of the cannula. When the user, having introduced the cannula under the skin 17 of a patient, places his thumb in the cavity, this causes that the entry aperture is directed towards the depth of the fatty tissue and not towards the skin of the patient, ensuring in this way a maintenance of the aperture in the fat to be sucked.

The compressed gas provided to cylinder 10 will provoke a backward and forward movement to piston 11 within the cylinder. Preferably, the movement of the piston is provoked by compressed gas in the two directions. It is also conceivable that the movement of the piston is provoked by compressed gas only in one direction, and that the movement in the other direction is ensured through a spring. The backward and forward motion has a frequency preferably ranging between approximately 10 to 500 Hz, in particular approximately 15 or 200 Hz. The used frequency is chosen according to the material used for the piston. Indeed, the resonance characteristics of the chosen material will influence the vibration wave. The chosen materials are for example ceramic or metal comprising for example stainless steel of aluminum. For stainless steel, a frequency of approximately 15 Hz is for example used.

The backward and forward frequency of the piston causes a vibration wave at the end of the cannula. A nutation movement is created in this way, comprising vibration component perpendicular to the axis of the cannula and a translation component according to the axis of the cannula. The amplitude of the translation component is less than 1 cm for limiting to the maximum extent lesions to vessels and nerves of the patient. In particular, the amplitude is in the order of 3 to 5 mm. It should be noted here that amplitudes of 2 and 6 mm are also comprised.

Figure 5:
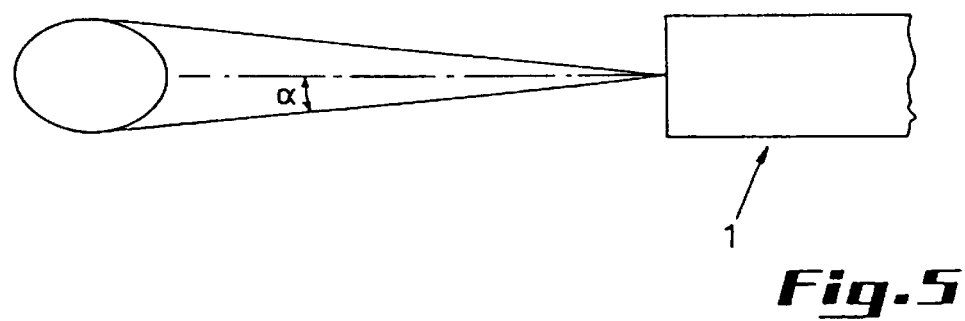
FIG. 5 schematically illustrates the nutation movement transmitted to the cannula.

The amplitude of the vibration component at the end of the cannula is according to the length of the cannula. The longer the cannula, the larger the amplitude of the vibration component at the end of the cannula. The length of the used cannulas is in the order of 5 to 35 cm. When using a cannula having a length of approximately 25 cm and a backward and forward frequency of 15 Hz, one can obtain an amplitude in the order of 1 cm at the free end of the cannula. This signifies that the free end of the cannula describes a nutation movement within a circle, such as illustrated in FIG. 5, wherein the circle has a diameter in the order of 2 cm. The size of the nutation movement can also be expressed as a nutation angle α such as illustrated in FIG. 5. In the case of a cannula of 25 cm and an amplitude of 1 cm, the angle α is in the order of 2,3°. The amplitude can also have an amplitude less than 1 cm, for example in the order of 3 to 5 mm.

Figure 4:
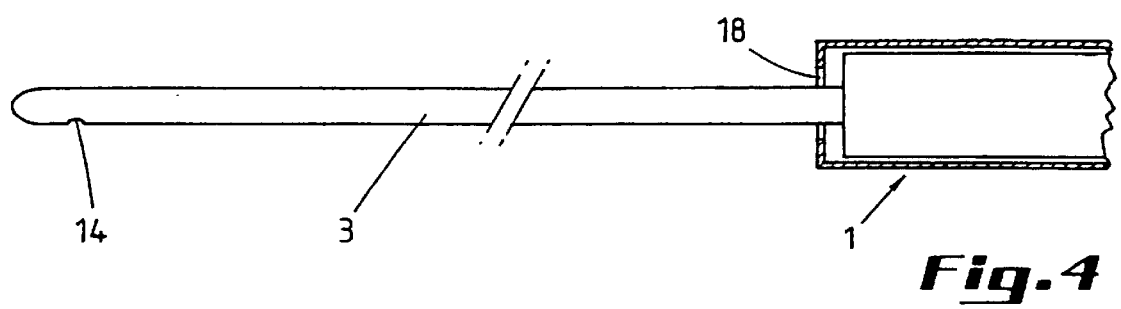
FIG. 4 is a section view of a portion of FIG. 3.

For allowing the nutation movement, a free space 18 is provided between the cannula and the handle, such as illustrated in FIG. 4 showing a section of a portion of the device according to FIG. 3.

In this way, the cannula 3 will receive the translation movement which is imposed not only when introducing the cannula under the skin of the patient, but also during the liposuction itself. Upon use, the vibration of the cannula is directly transmitted to the fat which is dissociated, dislocated or split and beats it so to speak in a foam which enables it to enter easily in apertures 14 of the cannula, thereby causing virtually no lesions of the vessels and the nerves of the patient. The translation allows to have the cannula penetrated easily under the skin, since the penetration movement, applied by the user, is assisted with the backward and forward motion of the cannula. By limiting considerably the lesion, the device can even be used under local aneasthesia, which is not the case with the known devices with mechanical assistance.

The user does not have necessarily to apply an intense massage nor pinching of the part to be treated, as with devices without mechanical assistance, since it is the vibration motion of the cannula which is transmitted to the fat and which provokes its dislocation and therefore its withdrawal to the entry aperture of the cannula. In practice, it is sufficient for the user to stretch the skin or to press the zone to be treated in order to compress the fat.

Since the user does not have necessarily to apply an intensive massage nor a pinching, he can concentrate on the guiding of the cannula at the locations where the fat has to be dislocated and removed. This allows thus the user to guide decently and with more precision the cannula under the skin of the patient. The hand of the user which holds the handle can work free in any direction of the space and impose the directions in this way to the cannula. In addition, the movement of the cannula, since it is mechanically assisted, is more precise and more regular.

In comparison to known mechanical assisted devices, the device according to the invention presents the advantage that it does not produce the guillotine effect, painful for the patient and provoked by the translation movement of the inner cannula with respect to the outer cannula.

Figure 9B:
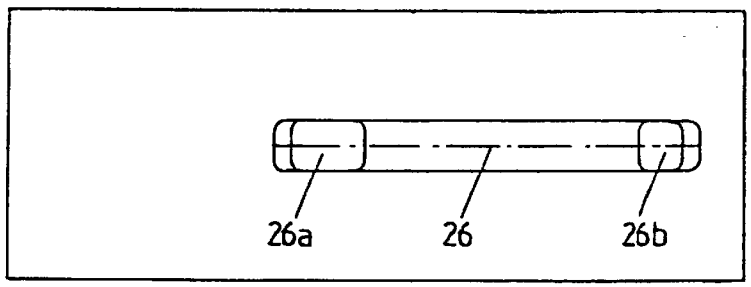
FIGS. 9a to e illustrate the configuration of admission and exhaust circuitry of the motor.
Figure 9A:
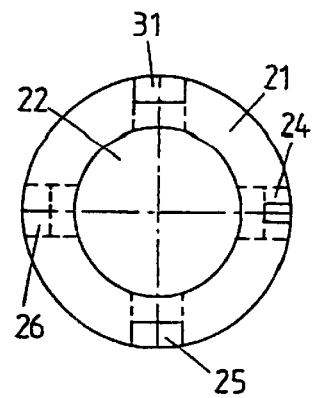
Figure 9C:
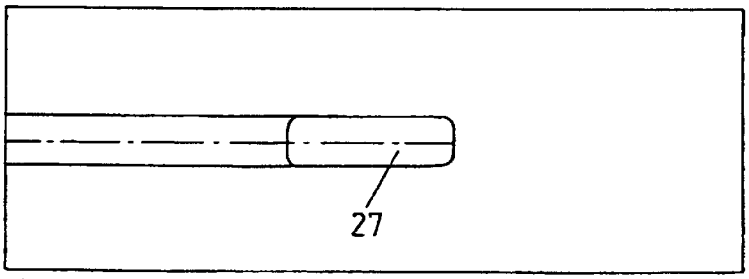
Figure 9D:
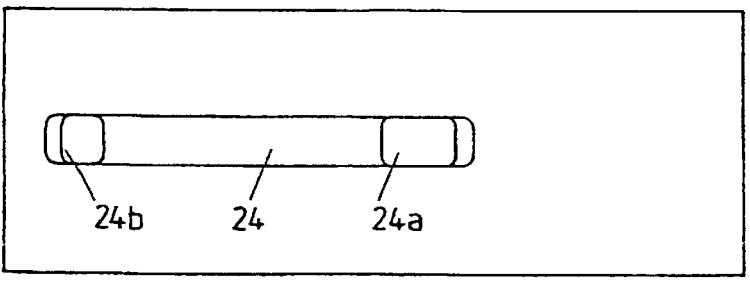
Figure 9E:
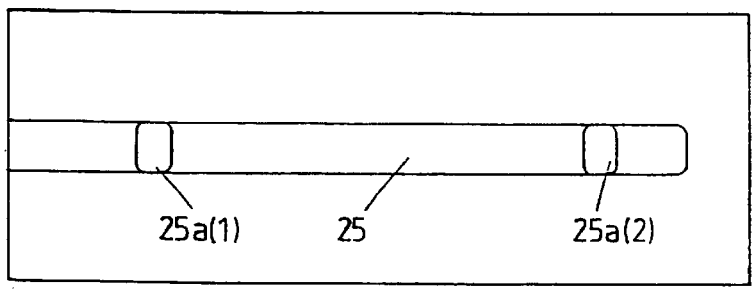

FIGS. 6 to 8 illustrate a longitudinal section view of a second embodiment of the drive member. This member 20 is also housed in housing 21 and comprises a piston 22 and also an admission and exhaust circuit illustrated more in detail in FIG. 9. The member comprises a gas admission circuit, preferably compressed air, at the front 26 and at the back 24, each having a front injector (24a, 26a) and a rear injector (24b, 26b) allowing to inject the gas in the circuit. The gas is supplied through an admission conduct 27 in connection with the injectors. The exhaust of the gas is ensured by an exhaust circuit having a front 25 and a rear 31 part. In FIGS. 6 to 8, the exhaust circuits are illustrated in the plane of the drawing whereas in reality they form an angle of 90° with the admission circuits. This has been done for rendering the description easier understandable and to better explain the functioning. FIG. 9a illustrates a cross-section view whereas FIGS. 9b to e illustrate each time longitudinal sections at the height of which the admission and exhaust circuits are situated. A selector 23 is housed in a cavity of the outer wall of piston 22. The movement of piston 22 inside the drive member is guided by means of bearings 28 and 29. The exhaust circuits 25 and 31 are connected to a pipe 30 allowing the release of the exhaust gas.

When the compressed gas is supplied to the admission conduct and the piston 22 is in initial backward position, such as illustrated in FIG. 6, the gas will penetrate through the front injector 24a in the rear admission circuit 24. Since the front injector 24a is located near the selector 23, the introduced gas will exert a pressure on the selector 23 causing in this way motion of the latter to the left or to the back of the member. The movement to the back of the selector 23 will further open the admission circuit 24 as illustrated in FIG. 7 where the selector is located in rear position.

The admission circuit 24 can now quickly be filled with compressed gas which will consequently flow to the back of the admission circuit 24. The movement of the selector has also opened the rear injector 24b causing in this way also an admission of compressed gas at the back of piston 22. The force exerted by the gas at the back of the piston will now cause its movement to the right or the front of the drive member. The movement of the piston causes in its turn that the gas present at the front of the piston will be pushed in the exhaust circuit 31.

When the piston 22 has traveled a sufficient path, it closes the admission to the exhaust circuit 31 as illustrated in FIG. 8. The gas remaining then in the space between the bearing 29 and the piston 22 will be compressed through the movement of the piston and dumps in this way the path of the piston. A pneumatic dumping device is obtained in this way which avoids that the piston strikes the bearing 29.

The movement to the front of the piston 22 will also compress the gas present in the front admission circuit 26, through the intermediary of the front injector 26b. The gas will circulate in this way in the front admission circuit 26 to reach the rear circuit. When arrived to this balance position, the unit is now in a configuration which will allow to leave in the opposed direction.

Since the compressed gas continues to arrive in the admission canal 27 and the injector 26a is free, the gas can enter the front admission circuit 26 and exert a pressure on the selector 23 pushing it to the front. The movement to the front of the selector will further open the front admission circuit 26 and the injector 26a, allowing the gas to travel in direction of the injector 26b and to fill the front admission circuit. The gas now present at the front of the piston 22 will exert a pressure on the latter and will push it to the back. This movement of the piston will cause in its turn that the gas present in the space between the bearing 29 and the piston will be pushed back in the circuit 24 and in the exhaust circuit 25 from which it reaches the piping 30.

When the piston 22 has traveled a sufficient path, it will close the exhaust circuit 25 and compress the gas in the space between the bearing 29 and the piston. In this way, the movement to the back of the piston is damped and the gas in said space functions as a damping device which avoids that the piston strikes the bearing 29. The gas in the rear admission circuit 24 is compressed and the initial position (FIG. 6) is found again, allowing to start again the movement.

The judicious position of the exhaust injectors has as effect to produce a damping at the end of the path, which limits the movement of the piston and avoids to strike the bearings. This function is also used as overpressure and allows to increase the compression of the gas in the admission circuit opposed to the exhaust circuit (31 to 24; 25 to 26). This reduces the filling time of the admission circuit for the next phase and allows to obtain in this way a higher working frequency and to save the gas consumption.

The movement of the piston is thus preceded by a movement of the selector which functions in phase opposition with respect to the movement direction of the piston.

The back and forth motion exerted by the piston 22 and the manner in which the compressed gas is fed to the piston will cause nutation movement of the cannula. The feeding with small quantities of compressed gas causing the back and forth motion of the piston drives also a bending movement on the axis of the piston. These two movements result then in a nutation movement. The piston tends also to exert a rotation movement which is however prevented due to the presence of a nose 32 at downstream side at the front of the piston.

According to an alternative, the drive member is provided to produce only a vibration movement instead of a combination of a vibration and translation movement.

According to the embodiment illustrated in FIG. 1, the fat, collected in the cannula, is collected laterally through the piping 6 and the container 7. According to an alternative, fat is collected, through the axis of the piston 11, which is in this case hollow. This considerably facilitate the evacuation of the fat, since it occurs in the extension of the cannula.

What is claimed is:

1. A liposuction device, comprising:
    a) sucking cannula means for sucking subcutaneous fat through an entry aperture, the sucking cannula means having defined therein said entry aperture and having a longitudinal axis;
    b) mechanical drive means for producing and transmitting a movement to the sucking cannula means and on which the sucking cannula means is mounted, the mechanical drive means having an entry for connecting an energy source thereto, and the movement of the sucking cannula means being a nutational movement which has a frequency ranging from 10 to 500 Hz and which comprises a vibrational component and a translational component, the vibrational component being perpendicular to the longitudinal axis of the sucking cannula means and the translational component being in line with the longitudinal axis of the sucking cannula means and having an amplitude ranging from 2 mm up to but less than 1 cm;
    c) a housing for housing the mechanical drive means; and
    d) a free space provided between the sucking cannula means and the housing, the free space being dimensioned in such a manner to allow the vibrational component of the nutational movement to dislocate subcutaneous fat in use.

2. The liposuction device according to claim 1, wherein the nutational movement produced by the mechanical drive means has a frequency of less than 150 Hz.

3. The liposuction device according to claim 2, wherein the nutational movement produced by the mechanical drive means has a frequency of about 15 Hz.

4. The liposuction device according to claim 1, further comprising a handle in which the mechanical drive means is housed.

5. The liposuction device according to claim 1, further comprising a control member for controlling starting and stopping of the mechanical drive means.

6. The liposuction device according to claim 5, wherein the liposuction device further comprises a handle in which the mechanical drive means is housed, and wherein the control member is a switch which is housed in the handle.

7. The liposuction device according to claim 5, wherein the control member is formed by a control pedal which cooperates with the mechanical drive means.

8. The liposuction device according to claim 1, wherein the energy source for the mechanical drive means comprises compressed air, and wherein the mechanical drive means comprises a pneumatic piston means for producing a back and forth motion.

9. The liposuction device according to claim 8, wherein the pneumatic piston means comprises a hollow axis connected to the sucking cannula means and provides for evacuation of dislocated subcutaneous fat.

10. The liposuction device according to claim 9, wherein the entry aperture is positioned at one side of the longitudinal axis of the sucking cannula means, and wherein the liposuction device has defined therein a cavity for a thumb positioned on another side of the longitudinal axis of the sucking cannula means.

* * * * *